United States Patent [19]
Zajaczkowski et al.

[11] Patent Number: 5,700,873
[45] Date of Patent: Dec. 23, 1997

[54] METHOD OF PREPARATION OF WATER-SOLUBLE COPOLYMER

[75] Inventors: Michael J. Zajaczkowski, Yoe; Barbara A. Stutzman, Dover, both of Pa.

[73] Assignee: Adhesives Research, Inc., Glen Rock, Pa.

[21] Appl. No.: 572,000

[22] Filed: Dec. 14, 1995

Related U.S. Application Data

[63] Continuation-in-part of Ser. No. 399,876, Mar. 7, 1995, Pat. No. 5,508,367.

[51] Int. Cl.$^6$ .................................................. C08F 271/02
[52] U.S. Cl. .................... 525/283; 525/296; 525/301; 526/73; 526/264; 526/303.1; 526/304; 526/318.4
[58] Field of Search ........................... 526/73; 525/283, 525/296, 301

[56] References Cited

U.S. PATENT DOCUMENTS

| | | | |
|---|---|---|---|
| 2,864,808 | 12/1958 | Harris | 526/73 |
| 2,983,717 | 5/1961 | Henley et al. | 526/73 |
| 3,575,911 | 4/1971 | Peterson | 524/340 |
| 3,732,193 | 5/1973 | Svarz | 526/217 |
| 3,948,866 | 4/1976 | Pennewiss et al. | 528/373 |
| 4,178,221 | 12/1979 | Boutin et al. | 522/4 |
| 4,361,687 | 11/1982 | Arndt et al. | 524/850 |
| 4,442,258 | 4/1984 | Sunakawa et al. | 524/767 |
| 4,897,458 | 1/1990 | Seelmann-Eggebert et al. | 526/318.3 |
| 5,314,977 | 5/1994 | Amick et al. | 526/286 |
| 5,319,020 | 6/1994 | Rosenski et al. | 524/762 |
| 5,326,644 | 7/1994 | Scholz et al. | 428/514 |
| 5,464,908 | 11/1995 | Sato et al. | 525/380 |
| 5,508,367 | 4/1996 | Zajaczkowski | 526/320 |

*Primary Examiner*—Mark Nagumo

[57] ABSTRACT

A method is provided for the production of a water-soluble or water-dispersible copolymer. The copolymer is comprised of a water-soluble base monomer and/or a water-soluble or water-dispersible macromer. The disclosed method involves a two step polymerization procedure wherein in a first step a minor portion of the reactants are polymerized to conversion under conditions which result in the formation of a low molecular weight product, and in a second step the remaining portion of the reactants are polymerized to conversion in the presence of the reaction product of the first step under conditions which result in the production of a higher molecular weight product.

29 Claims, No Drawings

METHOD OF PREPARATION OF WATER-SOLUBLE COPOLYMER

CROSS-REFERENCE TO RELATED APPLICATION

The present application is a continuation-in-part of U.S. patent application Ser. No. 08/399,876, filed Mar. 7, 1995, U.S. Pat. No. 5,508,367.

BACKGROUND OF THE PRESENT INVENTION

The present invention is directed to a method of preparation of water-soluble or water-dispersible copolymers.

Water-soluble polymers have a variety of end uses, including pressure sensitive adhesives, flocculants, paper-treating agents, sedimentation agents, filtration agents, thickening agents, etc.

It is, however, difficult to produce said polymers by conventional free radical polymerization procedures as the presence of a large amount of hydrophilic monomer(s) during polymerization undesirably results in the formation of a non-processable gel-like material. This problem is accentuated by the presence of a water-soluble or water-dispersible macromer in the event that a graft copolymer is being produced.

Various methods of preparing water-soluble polymers are disclosed in U.S. Pat. Nos. 2,864,808; 2,983,717; 3,575,911; 3,732,193; 3,948,866; 4,178,221; 4,361,687; 4,442,258; 4,897,458; 5,314,977; 5,319,020; and 5,464,908. Several of the methods described in these patents attempt to address the problems associated with the formation of a gel.

However, a need still exists for a method of preparation of a water-soluble or water-dispersible copolymer which enables such a copolymer to be prepared from hydrophilic monomers and/or macromers without formation of a gel.

OBJECTS AND SUMMARY OF THE PRESENT INVENTION

It is an object of the present invention to provide a novel method for producing a water-soluble or water-dispersible copolymer.

It is another object of the present invention to provide a novel method for producing a water-soluble or water-dispersible graft copolymer.

In accordance with one aspect of the present invention, there is thus provided a method for the production of a water-soluble or water-dispersible copolymer comprised of one or more water-soluble base monomers A and optionally one or more hydrophobic B monomers copolymerized with said A monomer, wherein said base monomer A comprises a vinyl monomer capable of forming a hydrophilic polymer, said method comprising the steps of (1) polymerizing to conversion under free radical polymerization conditions a minor portion of the total reaction mixture of said A and B monomers in the presence of a first polymerization initiator to produce a first reaction product, said first polymerization initiator under said polymerization conditions of step (1) having a half-life ranging from about 20–60 minutes, and (2) admixing the remaining major portion of the reaction mixture of said A and B monomers with said reaction product of step (1) and polymerizing said admixture to conversion under free radical polymerization conditions in the presence of a second polymerization initiator having a half-life at said polymerization conditions of step (2) of at least about 5 hours, said polymerization initiator being present in each of said steps (1) and (2) in an amount within the range of from about $10^{-1}$ to $10^{-4}$ moles/liter based on the total volume of the reactants.

In accordance with the present invention, there is also provided a method for the production of a water-soluble or water-dispersible graft copolymer comprised of one or more water-soluble base monomers A and a water-soluble or water-dispersible macromer C, and optionally one or more hydrophobic B monomers copolymerized with said A monomer, wherein said base monomer A comprises a vinyl monomer capable of forming a hydrophilic polymer, and said C macromer forming polymeric sidechains on said graft copolymer, said method including the steps of (1) polymerizing to conversion under free radical polymerization conditions a minor portion of the total reaction mixture of said A and B monomers and said macromer in the presence of a first polymerization initiator to produce a first reaction product, said first polymerization initiator under said polymerization conditions of step (1) having a half-life ranging from about 20–60 minutes, and (2) admixing the remainder of the reaction mixture of said A and B monomers and said macromer with said reaction product of step (1) and polymerizing said admixture to conversion under free radical polymerization conditions in the presence of a second polymerization initiator having a half-life at said polymerization conditions of step (2) of at least 5 hours, said polymerization initiator being present in each of said steps (1) and (2) in an amount within the range of from about $10^{-1}$ to $10^{-4}$ moles/liter based on the total volume of the reactants.

In accordance with yet another aspect of the present invention, there is also provided a method for the production of a water-soluble or water-dispersible graft copolymer comprised of one or more hydrophobic B monomers and a water-soluble or water-dispersible macromer C, said method including the steps of (1) polymerizing to conversion under free radical polymerization conditions a minor portion of the total reaction mixture of said B monomer and said macromer in the presence of a first polymerization initiator to produce a first reaction product, said first polymerization initiator under said polymerizations of step (1) having a half-life ranging from about 20–60 minutes, and (2) admixing the remainder of the reaction mixture of said B monomer and said macromer with said reaction product of step (1) and polymerizing to conversion said admixture under free radical polymerization conditions in the presence of a second polymerization initiator having a half-life at said polymerization conditions of step (2) of at least 5 hours, said polymerization initiator being present in each of said steps (1) and (2) in an amount with the range of from about $10^{-1}$ to $10^{-4}$ moles/liter based on the total volume of the reactants.

In accordance with a preferred embodiment of the above method, said base monomer A comprises a vinyl monomer capable of forming a hydrophilic polymer, and said macromer C forming polymeric sidechains on said graft copolymer comprises a hydrophilic macromer represented by the formula:

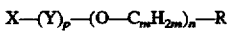

$$X-(Y)_p-(O-C_mH_{2m})_n-R$$

wherein X is a moiety copolymerizable with monomers A and/or B or capable of attachment to polymerized monomers A and/or B, Y is a divalent linking group, R is a terminal group; and in which m is an integer of from 2 to 6, n is an integer of from 5 to 300, and p is 0 or 1.

DETAILED DESCRIPTION OF THE INVENTION

The water-soluble or water-dispersible copolymer produced by the method of the present invention comprises at least one water-soluble base monomer and/or a hydrophilic macromer.

It has been found that the use of single stage free radical polymerization of one or more water-soluble monomers to provide a water-soluble polymer may yield a non-processable gel. It has been further found that by use of a multi-step free radical polymerization process employing differing polymerization conditions, a water-soluble or water-dispersible copolymer may be prepared while avoiding the formation of a non-processable gel.

Specifically, in the multi-step procedure of the present invention, a minor portion of the reactants are polymerized to conversion in step (1) at free radical polymerization conditions in the presence of a polymerization initiator having a sufficiently low half-life whereby the extent of polymerization of the reactants is limited such that the formation of a low viscosity low molecular weight polymer results. To accomplish the desired result of obtaining a low viscosity polymer, a polymerization initiator is employed having a relatively short half-life (i.e., from about 20–60 minutes) at the polymerization conditions employed. As a result of using a polymerization initiator in step (1) having a relatively short half-life at the polymerization conditions employed, the low molecular weight, low viscosity polymer product which is produced may serve as a solvent medium for the additional reactants added in the second step.

Once the low viscosity product is produced in the first step, the remaining major portion of reactants is admixed therewith. This admixture is then caused to further polymerize to conversion in the presence of a polymerization initiator having a longer half-life than that employed in the first step. The added reactants in the second step are caused to polymerize in the presence of the low viscosity polymer product of the first step, which effectively acts as a "solvent" for the polymerization reactants of the second step. Advantageously, a high molecular weight polymer product can thus be produced without the formation of a gel.

The second step is conducted in the presence of a second polymerization initiator having a half-life of at least 5 hours, and preferably from 5 to 10 hours, at the polymerization conditions employed in the second step. The product produced by the second step is a more viscous, higher molecular weight polymer than that resulting from the first step. The polymer product may be recovered by conventional methods to yield the desired copolymer product having the physical characteristics desired to be obtained.

In each of steps (1) and (2), the amount of polymerization initiator employed ranges from about $10^{-1}$ to $10^{-4}$ moles/liter based on the total volume of the reactants, and preferably within the range of from about $5 \times 10^{-2}$ to $10^{-4}$ moles/liter.

The novel method of the present invention may be used with a wide variety of reaction mixtures to form a water-soluble copolymer, as follows:

(1) a water-soluble A monomer and a water-soluble or water-dispersible macromer C;

(2) a water-soluble A monomer, a hydrophobic B monomer, and a water-soluble or water-dispersible macromer C;

(3) solely of water-soluble A monomers;

(4) water-soluble A monomers and hydrophobic B monomers; and (5) a hydrophobic B monomer and a water-dispersible or water-soluble macromer C.

Obviously, one or more of each of the A and B monomers and the macromer may be employed in the reaction mixture to yield the desired water-soluble copolymer.

As discussed above, in the method of the present invention, a minor portion (i.e., 40 percent or less) of the total reaction mixture is caused to polymerize to conversion to step (1). A major portion of the reaction mixture (i.e., at least 60 percent by weight) is admixed with the reaction product of step (1) and caused to polymerize to conversion in step (2). The portion of the total reaction mixture polymerized in step (1) generally ranges from about 10–40 percent by weight of the total reaction mixture. For macromer-containing reaction mixtures, from about 15–30 weight percent of the reaction mixture is preferably employed in step (1). For non-macromer-containing reaction mixtures, from about 10–20 percent by weight of the reaction mixture is preferably employed in step (1). It is desirable to react as much of the reaction mixture as possible in step (2) while reacting in step (1) only an amount of the reactants sufficient to provide an effective solvating medium for the step (2) reactants.

Exemplary free radical polymerization initiators for use in the present invention include but are not limited to VAZO 52 (2,2'-azobis(2,4-dimethylpentanenitrile)), VAZO 64 (2,2'-azobis(2-methylpropanenitrile)), VAZO 67 (2,2'-azobis (2-methylbutanenitrile)), and VAZO 88 (1,1'-azobis (cyclohexanecarbonitrile)), each a product of DuPont. Benzoyl peroxide may also be employed as a polymerization initiator.

The half-life characteristics of such initiators in relation to a reaction temperature is well-known to those skilled in the art. By way of example, the respective half-life of the above initiators at a temperature of 70° C. is approximately as follows: VAZO 52 (45 minutes), VAZO 64 (280 minutes), VAZO 67 (400 minutes), VAZO 88 (8000 minutes) and benzoyl peroxide (438 minutes). With regard to the present invention, given the presence of from $10^{-1}$ to $10^{-4}$ moles/liter of the polymerization initiator in the reaction zone, one skilled in the art can readily determine the reaction temperature to be employed in both steps (1) and (2) based on the desired half-life required. For example, VAZO 52 exhibits a half-life of approximately 45 minutes at 70° C. Accordingly, use of a reaction temperature of 70° C. in step (1) will enable step (1) to be practiced in accordance with the present invention when the VASO 52 initiator is employed. A half-life of at least 5 hours may be achieved in step (2) by use of either of VAZO 67, VAZO 88 or benzoyl peroxide if a polymerization temperature such as 70° C. is employed.

Suitable water-soluble base monomer(s) A comprise a vinyl monomer capable of forming a hydrophilic polymer. In general, such monomers comprise hydroxy(lower)alkyl acrylates, hydroxy(lower)alkyl methacrylates, dihydroxy (lower)alkyl methacrylates, etc. Exemplary water-soluble base monomers include but are not limited to hydroxyethyl acrylate, hydroxypropyl acrylate, hydroxybutyl acrylate, hydroxybutyl methacrylate, as well as alkyl vinyl ethers and hydroxy alkyl vinyl ethers (wherein the alkyl group has up to 5 carbon atoms).

Additional hydrophilic A monomers include water-soluble vinyl monomers having at least one nitrogen atom. Such monomers include but are not limited to N-monosubstituted acrylamides such as acrylamide, methacrylamide, N-methylacrylamide, N-ethylacrylamide, N-methylolacrylamide, N-hydroxyethylacrylamide, and diacetone acrylamide; N,N-disubstituted acrylamides such as N,N-dimethylacrylamide, N,N-diethylacrylamide, N-ethyl-N-aminoethyl acrylamide, N-ethyl-N-hydroxyethylacrylamide, N,N-dimethylolacrylamide, and N,N-dihydroxyethylacrylamide, etc.

Other suitable A monomers include, for example, various hydrophilic vinyl monomers such as acrylic and methacrylic acid, glycerol acrylate or methacrylate, hydroxyethyl methacrylate, hydroxypropyl methacrylate, vinyl pyrrolidone and vinyl caprolactam.

The macromer C, if present, forms polymeric sidechains on the graft copolymer. The macromer C is hydrophilic by nature (i.e., the macromer is water-soluble or water-dispersible).

The macromer may be represented by the formula X—(Y)$_p$—Z—R wherein X is a moiety copolymerizable with monomers A and B or, in the alternative, capable of attachment to polymerized monomers A and B, Y is a divalent linking group, Z is a water-soluble or water-dispersible homo- or polymeric moiety essentially unreactive at copolymerization conditions, R is a terminal group, and p is 0 or 1.

More specifically, the X moiety is an unsaturated polymerizable moiety the composition of which is not critical. The X moiety may be, for example, when intended to be copolymerizable with monomers A and B, simply a vinyl group of the formula CHR=CR$^1$— where R is hydrogen or COOH and R$^1$ is hydrogen or alkyl such as methyl. Other exemplary X moieties include but are not limited to methacryloyl, maleoyl, itaconoyl, crotonoyl, unsaturated urethane moiety, methacrylamido and moieties of the formula CH$_2$=CHCH$_2$O—.

The X moiety may comprise an amine or alcohol moiety (such as a monohydroxyl or monoamine moiety) which permits attachment of the macromer to a suitable functionality on previously-polymerized monomers A and B. For instance, the hydroxyl moiety can serve as a terminal reactive group by reaction with suitable moieties on the polymer backbone resulting from the use of monomers such as isocyanate-substituted (meth)acrylic acid, (meth)acrylic acid anhydride, etc.

A preferred Y divalent linking group is

or a linking group which incorporates such a moiety.

Additional Y linking groups which may be employed in connection with the present invention include but are not limited to the following moieties:

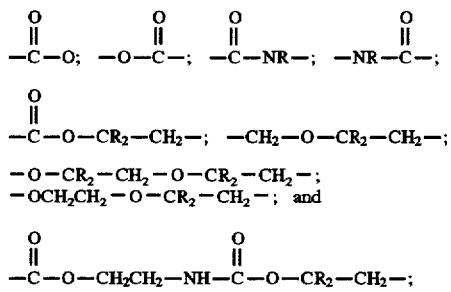

where R is hydrogen, alkyl or phenyl. Obviously, the presence of the Y linking group is optional in the event the moiety includes a functionality which enables the Z moiety to react with the X moiety. As the incorporation of macromolecular moieties in copolymers is well understood by those skilled in the art, the choice of a suitable X and Y moiety for use in the present invention may be readily made upon practice of the present invention. See, for example, the discussion in U.S. Pat. Nos. 3,786,116; 3,832,423; 3,842,058; 3,842,059; 3,842,146; and 4,554,324, herein incorporated by reference.

The Z moiety is preferably selected from the group consisting of (but not limited to) a polypropylene or polyethylene oxide radical, a polyethyloxazoline radical such as a radical of poly(2-ethyl-2-oxazoline), polyacrylic acid radical, polyvinyl alcohol radical, polyvinylpyrrolidone radical, polyvinyl caprolactam radical, polymethylvinyl ether radical or mixtures thereof. Exemplary C macromers formed from such radicals include but are not limited to ethoxylated or propoxylated hydroxy(lower)alkyl meth (acrylate) and polymethylvinyl ether mono(meth)acrylate. The molecular weight of the macromer used in the present invention is not critical but will generally range from about 300 to about 50,000, and preferably from about 300 to 3,000.

The hydrophilic macromer C is more preferably represented by the formula:

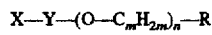

wherein X and Y are as defined above and R represents a terminal group; and in which m is an integer of from 2 to 6 and n is an integer of from 5 to 300. More specifically, macromer C is advantageously an ethoxylated or propoxylated hydroxy(lower)alkyl (meth)acrylate represented by the formula:

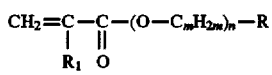

wherein R$_1$ is hydrogen or C$_{1-5}$ alkyl and R is a terminal group. Preferably, m is 2 or 3 and n is 5 to 30, and R is OH or C$_{1-5}$ alkyl.

The Z moiety is preferably comprised solely of one or more hydrophilic monomer radicals to ensure that the resulting macromer is water-soluble or water-dispersible. However, the Z moiety may also be a copolymer of hydrophilic and hydrophobic monomers, with any copolymerized hydrophobic portion being present in an amount insufficient to render the resulting macromer water-insoluble or non-water-dispersible. Desirably, any non-hydrophilic portion employed in such a copolymer is present in an amount of less than 50 percent by weight based on the weight of the macromer, and preferably less than 30 percent by weight.

The macromer C may employ a variety of terminal groups R. While the terminal group may typically be OH or C$_{1-5}$ alkyl, it may be desirable to select a terminal group based on the functional character of the terminal group. For instance, suitable terminal groups include but are not limited to (1) acid/ionic groups such as carboxyl, phosphate or sulfate groups, (2) hydrophobic groups such as lower alkyl, phenyl or substituted phenyl, and (3) hydrophilic groups such as hydroxyl or amine groups.

Depending upon the terminal group employed, ionic end groups may be used to provide pH-dependent solubility characteristics for the copolymer. Hydrophobic terminal groups may be used to reduce the water solubility of the copolymer.

Other physical properties or characteristics of the copolymer may be modified by selection of suitable terminal groups. Ionic terminal groups may be used to provide a desired degree of cross-linking; for example, by neutralizing acid moieties with metal hydroxides. High temperature performance may be enhanced by incorporating an acid functionality in conjunction with a ditertiary amine. Aqueous solution viscosities may be influenced by the presence of ionic terminal groups.

As discussed above, one or more polymerizable hydrophobic B monomers may be incorporated in the copolymer which B monomer(s) is copolymerizable with the A monomer, either alone with the A monomer or together with the hydrophilic macromer. It is preferable for the B monomer to be present in an amount of 25 percent by weight or less, and most preferably 20 percent by weight or less.

Exemplary hydrophobic B monomers include monomeric acrylic or methacrylic acid esters of a non-tertiary alcohol having from 4–12 carbon atoms on average, and preferably from 4–8 carbon atoms, such as methyl acrylate or methacrylate, ethyl acrylate or methacrylate, and propyl acrylate or methacrylate.

The respective amounts of the monomers A and B and the macromer C used in the reaction mixture may vary widely, with the sole requirement being that the water-soluble or hydrophilic component(s) be present in an amount sufficient to ensure that the copolymer produced is water-soluble or water-dispersible.

By way of example, in a graft copolymer composition, the A monomer is preferably present in an amount of from 25 to 70 percent by weight, said optional B monomer is present in an amount of from 0 to 40 percent by weight, and said C macromer is present in an amount of from 10 to 65 percent by weight, and preferably 30 to 60 percent by weight, based on the total weight of the respective components A, B and C in the composition.

If no C macromer is present, the B monomer may be present in an amount up to 40 percent by weight based on the total weight of A and B monomers, preferably up to 30 percent by weight. If the water-soluble C macromer is present together with only the B monomer, the B monomer may be present in an amount of up to about 65 percent by weight depending if the macromer is sufficiently water-soluble to ensure that the resulting copolymer is water soluble.

Apart from achieving the necessary water-soluble or water-dispersible character for the copolymer, the respective A and B monomers and C macromer may be present in respective amounts necessary to attain the desired end use for the copolymer. For instance, water-soluble copolymers have a variety of end uses, and may be tailored to enable the copolymer to function as flocculating agents, filtration agents, thickening agents, sedimentation agents, and pressure sensitive adhesives.

The invention will be discussed in conjunction with the following examples, which are merely illustrative of the present invention and not intended to in any way limit the scope of the invention.

EXAMPLE 1

180.13 grams of ethyl acetate and 120.09 grams of isopropyl alcohol (as solvents) were charged to a 1-liter reaction vessel. To the charged material, 18.33% of the monomers identified below were added. Under a nitrogen atmosphere, the batch was heated to 71°–77° C. and 1.27 grams of VAZO-52 (polymerization initiator having a half-life of approximately 35–40 minutes at the reaction temperature employed) were added. The reactants were allowed to polymerize for 20 minutes to produce a low viscosity polymer capable of solvating the remaining reactants. Single stage polymerization was found to yield a non-processable gel, which result is avoided by the two-step polymerization of the present invention. The remaining 81.67% of the monomer mix along with 0.75 grams of benzoyl peroxide (having a half-life of 8 hours at the reaction temperature) were added to the reaction mix over 2 hours while maintaining a reaction temperature of 71°–77° C. The reactants were polymerized until all monomers were consumed. The reactor feed mix consisted of the following components:

|  | Amount (Grams) |
|---|---|
| Monomers |  |
| HEMA-10 (macromer) | 114.09 |
| HEMA-5 (macromer) | 26.34 |
| Hydroxy Ethyl Acrylate (A monomer) | 83.88 |
| Hydroxy Propyl Acrylate (A monomer) | 100.67 |
| Acrylamide (A Monomer) | 9.06 |
| Solvents |  |
| Ethyl acetate | 180.13 |
| Isopropyl alcohol | 120.09 |

Note:
HEMA-5, 10 are 5 and 10 mole ethoxylates of hydroxy ethyl methacrylate (produced by BIMAX, INC.)
VAZO-52: Dupont trade name for free radical initiator 2,2'-azobis (2,4-dimethylpentanenitrile).
A water-soluble graft copolymer was thus produced.

EXAMPLE 2

The procedure of Example 1 was repeated using the following reactor feed components to produce a tackifier-free water-soluble copolymer having pressure sensitive adhesive properties:

|  | Amount (Grams) |
|---|---|
| Monomers |  |
| HEMA-10 (macromer) | 134.22 |
| Hydroxy Ethyl Acrylate (A monomer) | 97.31 |
| Acrylamide (A monomer) | 9.06 |
| Butyl Acrylate (B monomer) | 57.04 |
| Vinyl Pyrrolidone (A monomer) | 20.13 |
| Acrylic Acid (A monomer) | 13.42 |
| Solvents |  |
| Ethyl acetate | 150.11 |
| Isopropyl alcohol | 150.11 |

EXAMPLE 3

The procedure of Example 1 was repeated using the following reactor feed components to produce a tackifier-free water-soluble copolymer having pressure sensitive adhesive properties:

|  | Amount (Grams) |
|---|---|
| Monomers |  |
| HEHA-10 (macromer) | 113.50 |
| Hydroxy Ethyl Acrylate (A monomer) | 107.38 |
| Acrylamide (A monomer) | 6.56 |
| Butyl Acrylate (B monomer) | 54.73 |
| Vinyl Pyrrolidone (A monomer) | 40.25 |
| Acrylic Acid (A monomer) | 13.12 |
| Solvents |  |
| Ethyl acetate | 180.13 |
| Isopropyl alcohol | 120.09 |

EXAMPLE 4

The procedure of Example 1 was repeated using the following reactor feed components to produce a tackifier-free water-soluble copolymer having pressure sensitive adhesive properties:

| Monomers | Amount (Grams) |
|---|---|
| HEMA-10 (macromer) | 134.22 |
| Hydroxy Ethyl Acrylate (A monomer) | 97.31 |
| Hydroxy Propyl Acrylate (A monomer) | 40.27 |
| Acrylamide (A monomer) | 10.06 |
| Butyl Acrylate (B monomer) | 23.56 |
| Vinyl Pyrrolidone (A monomer) | 10.06 |
| Acrylic Acid (A monomer) | 10.06 |
| Solvents | |
| Ethyl acetate | 160.11 |
| Isopropyl alcohol | 140.11 |

EXAMPLE 5

The procedure of Example 1 was repeated using the following reactor feed components to produce a tackifier-free water-soluble copolymer having pressure sensitive adhesive properties:

| Monomers | Amount (Grams) |
|---|---|
| HEMA-10 (macromer) | 268.43 |
| Hydroxy Ethyl Acrylate (A monomer) | 181.20 |
| Hydroxy Propyl Acrylate (A monomer) | 181.20 |
| Acrylamide (A monomer) | 20.13 |
| Acrylic Acid (A monomer) | 20.13 |
| Solvents | |
| Ethyl Acetate | 345.25 |
| Isopropyl Alcohol | 255.19 |

EXAMPLE 6

94.5 grams of ethyl acetate and 130.5 grams of isopropyl alcohol (or solvents) were charged to a 1-liter reaction vessel. To the charge, 18.33% of the monomers identified below were added. Under a nitrogen atmosphere, the batch was heated to 71°–77° C. and 0.94 grams of VAZO-52 (half-life of 35–40 minutes at reaction temperature) were added. The reactants were allowed to polymerize for 20 minutes. The remaining 81.67% of the monomer mix along with 0.50 grams of benzoyl peroxide (half-life of 8 hours at reaction temperature) were added to the reaction mix over 1 hour while maintaining a reaction temperature of 71°–77° C. The reactants were polymerized until all monomers were consumed (123.75 grams of isopropyl alcohol were added to reduce viscosity). The monomer feed consisted of the following:

| Monomers | % of Monomers | Amount (Grams) |
|---|---|---|
| HEMA-10 (macromer) | 38.13 | 90.00 |
| 2-Ethyl-2-Oxazoline (macromer) | 4.66 | 11.00 |
| Hydroxy Ethyl Acrylate (A monomer) | 23.83 | 56.25 |
| Hydroxy Propyl Acrylate (A monomer) | 10.97 | 25.88 |
| Vinyl Pyrrolidone (A monomer) | 4.77 | 11.25 |
| Vinyl Caprolactam (A monomer) | 4.77 | 11.25 |
| Butyl Acrylate (B monomer) | 12.87 | 30.37 |

EXAMPLE 7

The procedure of Example 6 was repeated with the exception that the 2-ethyl-2-oxazoline macromer was not employed:

| Solvents | Amount (Grams) |
|---|---|
| Ethyl Acetate | 189.00 |
| Isopropyl Alcohol | 261.00 |

| Monomers | % of Monomers | Amount (Grams) |
|---|---|---|
| HEMA-10 (macromer) | 40.00 | 179.98 |
| Hydroxy Ethyl Acrylate (A monomer) | 25.00 | 12.50 |
| Hydroxy Propyl Acrylate (A monomer) | 11.50 | 52.29 |
| Vinyl Pyrrolidone (A monomer) | 5.00 | 22.55 |
| Vinyl Caprolactam (A monomer) | 5.00 | 22.55 |
| Butyl Acrylate (B monomer) | 13.50 | 60.76 |

EXAMPLE 8

Ethyl acetate (25 grams) and isopropyl alcohol (75 grams) (as solvents) were charged to a reaction vessel. To the charge, 19.86% of the monomers identified below were added. Under a nitrogen atmosphere, the batch was heated to 70–73° C. and 0.94 grams of VAZO-52 (half-life of 35–40 minutes at reaction temperature) were added together with 100 grams of additional solvent mixture. The reactants were allowed to polymerize for 20 minutes. The remaining 80.14% of the monomer mix along with benzoyl peroxide initiator (half-life of 8 hours at reaction temperature) were added to the reaction mix over 1 hour while maintaining a reaction temperature of 70°–73° C. The reactants were polymerized until all monomers were consumed. The monomer feed consisted of the following:

| Monomers | % of Monomers | Amount (Grams) |
|---|---|---|
| HEMA-10 (macromer) | 40.00 | 90.00 |
| HEMA-5 | 5.00 | 11.00 |
| Hydroxy Ethyl Acrylate (A monomer) | 22.75 | 56.25 |
| Hydroxy Propyl Acrylate (A monomer) | 8.75 | 25.88 |
| Vinyl Pyrrolidone (A monomer) | 3.50 | 11.25 |
| Vinyl Caprolactam (A monomer) | 3.50 | 11.25 |
| Butyl Acrylate (B monomer) | 15.00 | 30.37 |
| Acrylic acid (A monomer) | 1.50 | |

What is claimed is:

1. A method for the production of water-soluble or water dispersible graft copolymer comprised of one or more water soluble base monomers A and at least one water soluble or water dispersible macromer C, and optionally one or more hydrophobic B monomers, wherein said base monomer A comprises a vinyl monomer capable of forming a hydrophilic polymer, and said C macromer forming polymeric side chains on said graft copolymer, said method comprising the steps of (1) polymerizing to conversion under free radical polymerization conditions from about 15 to 30 percent by weight of the total reaction mixture of said A and B monomers and said macromer in the presence of a first polymerization initiator to produce a first reaction product, said first polymerization initiator under said polymerization conditions of step (1) having a half-life of from about 20 to 60 minutes, and (2) admixing the remainder of the reaction mixture with the product of step (1) and polymerizing to conversion said admixture at free radical polymerization conditions in the presence of a second polymerization initiator having a half-life of at least about 5 hours at said polymerization conditions of step (2), and each said polymerization initiator being present in each of said steps (1) and (2) in an amount within the range of from about $10^{-1}$ to $10^{-4}$ moles/liter based on the total volume of the reactants.

2. The method of claim 1 wherein said A monomer is present in an amount of from 25 to 70 percent by weight, said B monomer is present in an amount of from 0 to 40 percent by weight, and said C macromer is present in an amount of from 10 to 65 percent by weight, based on the total weight of the respective components A, B and C.

3. The method of claim 1 wherein said A monomer is selected from the group consisting of hydroxy(lower)alkyl acrylates, hydroxy(lower)alkylmethacrylates, dihydroxy (lower)alkylacrylates, dihydroxy(lower)alkyl methacrylates and mixtures thereof.

4. The method of claim 1 wherein said A monomer is a water-soluble vinyl monomer having at least one nitrogen atom.

5. The method of claim 4 wherein said A monomer is selected from the group consisting of acrylamide, methacrylamide, N-methylacrylamide, N-ethylacrylamide, N-methylolacrylamide, N-hydroxyethylacrylamide, diacetone acrylamide, N,N-dimethylacrylamide, N,N-diethylacrylamide, N-ethyl-N-aminoethyl acrylamide, N-ethyl-N-hydroxyethylacrylamide, N,N-dimethylolacrylamide, N,N-dihydroxyethylacrylamide and mixtures thereof.

6. The method of claim 1 wherein said A monomer is a vinyl monomer selected from the group consisting of acrylic and methacrylic acid, vinyl pyrrolidone, vinyl caprolactam and mixtures thereof.

7. The method of claim 1 wherein said macromer is defined by the formula $X-(Y)_p-Z-R$, wherein X is a moiety copolymerizable with monomers A and B or capable of attachment to copolymerized monomers A and B, Y is a divalent linking group, Z is a water-soluble or water-dispersible homo- or copolymeric moiety, R is a terminal group, and p is 0 or 1.

8. The method of claim 7 wherein X is a (meth)acrylate moiety.

9. The method of claim 7 wherein Z is selected from the group consisting of a polyalkylene oxide radical, a polyethyloxazoline radical, a polyacrylic acid radical, a polyvinyl alcohol radical, a polyvinylpyrrolidone radical, a polyvinylcaprolactam radical and a polymethylvinyl ether radical.

10. The method of claim 1 wherein said macromer is defined by the formula:

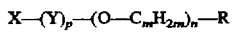

wherein X is a moiety copolymerizable with monomers A and B or capable of attachment to copolymerized monomers A and B, Y is a divalent linking group, R is a terminal group, m is an integer of from 2 to 6, n is an integer of from 5 to 300, and p is 0 or 1.

11. The method of claim 10 wherein the macromer is defined by the formula

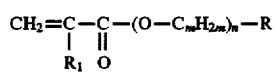

wherein $R_1$ is hydrogen or $C_{1-5}$ alkyl and R is a terminal group.

12. The method of claim 11 wherein R is OH or $C_{1-5}$ alkyl.

13. The method of claim 1 wherein said macromer is selected from the group consisting of ethoxylated hydroxy-alkyl meth(acrylate), poly(2-ethyl-2-oxazoline), polyacrylic acid, polyvinyl alcohol, polyvinylpyrrolidone, polyvinyl caprolactam and polymethylvinyl ether mono(meth) acrylate.

14. The method of claim 1 wherein any B monomer present comprises a monomeric acrylic or methacrylic acid ester of a non-tertiary alcohol having from 4–12 carbon atoms on average.

15. A method for the production of a water-soluble or water-dispersible copolymer comprised of one or more water-soluble base monomers A and optionally one or more hydrophobic B monomers copolymerized with said A monomer, wherein said base monomer A comprises a vinyl monomer capable of forming a hydrophilic polymer, said method comprising the steps of (1) polymerizing to conversion under free radical polymerization conditions a minor portion of the total reaction mixture of said A and B monomers in the presence of a first polymerization initiator to produce a first reaction product, said first polymerization initiator under said polymerization conditions of step (1) having a half-life ranging from about 20–60 minutes, and (2) admixing the remaining major portion of the reaction mixture of said A and B monomers with said reaction product of step (1) and polymerizing said admixture to conversion under free radical polymerization conditions in the presence of a second polymerization initiator having a half-life at said polymerization conditions of step (2) of at least about 5 hours, each said polymerization initiator being present in each of said steps (1) and (2) in an amount within the range of from about $10^{-1}$ to $10^{-4}$ moles/liter based on the total volume of the reactants.

16. The method of claim 15 wherein said A monomer is selected from the group consisting of hydroxy(lower)alkyl acrylates, hydroxy(lower)alkylmethacrylates, dihydroxy (lower)alkylacrylates, dihydroxy(lower)alkyl methacrylates and mixtures thereof.

17. The method of claim 15 wherein said A monomer is a water-soluble vinyl monomer having at least one nitrogen atom.

18. The method of claim 17 wherein said A monomer is selected from the group consisting of acrylamide, methacrylamide, N-methylacrylamide, N-ethylacrylamide, N-methylolacrylamide, N-hydroxyethylacrylamide, diacetone acrylamide, N,N-dimethylacrylamide, N,N-diethylacrylamide, N-ethyl-N-aminoethyl acrylamide, N-ethyl-N-hydroxyethylacrylamide, N,N-dimethylolacrylamide, N,N-dihydroxyethylacrylamide and mixtures thereof.

19. The method of claim 15 wherein said A monomer is a vinyl monomer selected from the group consisting of acrylic and methacrylic acid, vinyl pyrrolidone, vinyl caprolactam and mixtures thereof.

20. The method of claim 15 wherein any B monomer present comprises a monomeric acrylic or methacrylic acid ester of a non-tertiary alcohol having from 4–12 carbon atoms on average.

21. A method for the production of a water-soluble or water-dispersible graft copolymer comprised of one or more hydrophobic B monomers and one or more water-soluble or water-dispersible macromers C, said method including the steps of (1) polymerizing to conversion under free radical polymerization conditions a minor portion of the total reaction mixture of said B monomer and said macromer in the presence of a first polymerization initiator to produce a first reaction product, said first polymerization initiator under said polymerization conditions of step (1) having a half-life ranging from about 20–60 minutes, and (2) admixing the remainder of the reaction mixture of said B monomer and said macromer with said reaction product of step (1) and polymerizing to conversion said admixture under free radical polymerization conditions in the presence of a second polymerization initiator having a half-life at said polymerization conditions of step (2) of at least 5 hours, each said polymerization initiator being present in each of said steps. (1) and (2) in an amount with the range of from about $10^{-1}$ to $10^{-4}$ moles/liter based on the total volume of the reactants.

22. The method of claim 21 wherein said macromer is defined by the formula $X-(Y)_p-Z-R$, wherein X is a moiety copolymerizable with monomers A and B or capable of attachment to copolymerized monomers A and B, Y is a divalent linking group, Z is a water-soluble or water-dispersible homo- or copolymeric moiety, R is a terminal group, and p is 0 or 1.

23. The method of claim 22 wherein X is a (meth)acrylate moiety.

24. The method of claim 22 wherein Z is selected from the group consisting of a polyalkylene oxide radical, a polyethyloxazoline radical, a polyacrylic acid radical, a polyvinyl alcohol radical, a polyvinylpyrrolidone radical, a polyvinylcaprolactam radical and a polymethylvinyl ether radical.

25. The method of claim 21 wherein said macromer is defined by the formula:

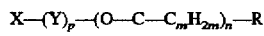

wherein X is a moiety copolymerizable with monomers A and B or capable of attachment to copolymerized monomers A and B, Y is a divalent linking group, R is a terminal group, m is an integer of from 2 to 6, n is an integer of from 5 to 300, and p is 0 or 1.

26. The method of claim 25 wherein the macromer is defined by the formula

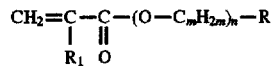

wherein $R_1$ is hydrogen or $C_{1-5}$ alkyl and R is a terminal group.

27. The method of claim 26 wherein R is OH or $C_{1-5}$ alkyl.

28. The method of claim 21 wherein said macromer is selected from the group consisting of ethoxylated hydroxyalkyl meth(acrylate), poly(2-ethyl-2-oxazoline), polyacrylic acid, polyvinyl alcohol, polyvinylpyrrolidone, polyvinyl caprolactam and polymethylvinyl ether mono(meth) acrylate.

29. The method of claim 21 wherein any B monomer present comprises a monomeric acrylic or methacrylic acid ester of a non-tertiary alcohol having from 4–12 carbon atoms on average.

* * * * *